(12) United States Patent
Ikeuchi et al.

(10) Patent No.: US 6,337,416 B2
(45) Date of Patent: Jan. 8, 2002

(54) PREPARATION OF (POLYCYCLIC SECONDARY-AMINO)DIALKOXYSILANE

(75) Inventors: Hiroyuki Ikeuchi; Yasuhisa Sakakibara, both of Chiba; Masayoshi Oue, Yamaguchi, all of (JP)

(73) Assignee: Ube Industries, Ltd., Yamaguchi (JP)

( * ) Notice: Subject to any disclaimer, the term of this patent is extended or adjusted under 35 U.S.C. 154(b) by 0 days.

(21) Appl. No.: 09/879,280

(22) Filed: Jun. 12, 2001

(30) Foreign Application Priority Data

Jun. 12, 2000 (JP) .......................................... 12-174740
Feb. 7, 2001 (JP) .......................................... 13-030886

(51) Int. Cl.$^7$ .............................. C07F 7/08; C07F 7/18; C07F 7/10
(52) U.S. Cl. ...................................... 556/471; 556/413
(58) Field of Search ........................... 556/471; 536/413

(56) References Cited

U.S. PATENT DOCUMENTS

| | | | | | |
|---|---|---|---|---|---|
| 5,808,123 | A | * | 9/1998 | Balduf et al. | 556/413 |
| 5,939,573 | A | * | 8/1999 | Ikai et al. | 556/413 |
| 5,994,573 | A | * | 11/1999 | Tachikawa et al. | 556/413 X |
| 6,114,558 | A | * | 9/2000 | Larson et al. | 556/413 |

* cited by examiner

*Primary Examiner*—Paul F. Shaver
(74) *Attorney, Agent, or Firm*—Reed Smith LLP

(57) ABSTRACT

A (polycyclic secondary-amino)dialkoxysilane favorably employable as a catalyst for polymerization of α-olefin can be prepared by reacting tetrachlorosilane, or a mono($C_1$–$C_8$) alkyltrichlorosilane with a polycyclic secondary-amine in a non-hydrous, non-alcoholic organic solvent in the presence of a hydrogen chloride-trapping reagent, to produce a (polycyclic secondary-amino)chlorosilane and reacting the (polycyclic secondary-amino)chlorosilane with an alkali metal alkoxide or an alkaline earth metal alkoxide in the presence of a lower alcohol.

8 Claims, No Drawings

PREPARATION OF (POLYCYCLIC SECONDARY-AMINO)DIALKOXYSILANE

CROSS-REFERENCES TO RELATED APPLICATIONS

This application claims Paris Convention priority of Japanese Application Nos. 2000-174740 filed Jun. 12, 2000 and 2001-030886 filed Feb. 7, 2001, the complete disclosure of which are hereby incorporated by reference.

FIELD OF THE INVENTION

The present invention relates to a process for preparing (polycyclic secondary amino)dialkoxysilanes.

BACKGROUND OF THE INVENTION

A great number of silane compounds have been proposed as catalyst components for enhancing stereoregularity in the polymerization of α-olefins. Particularly, (polycyclic secondary-amino)dialkoxysilanes have been known as good catalyst components and paid attention.

U.S. Pat. No. 5,939,573 (issued Aug. 17, 1999) describes a process for the preparation of di(polycyclic amino) dimethoxysilanes utilizing Grignard reaction. The Grignard reaction requires a specific reaction solvent such as a dialkyl ether or a cyclic ether. Further, it is required to frequently treat by-produced magnesium methoxyhalide with extraction in the course of the reaction for recovering the target product.

Japanese Patent Provisional Publication No. 11-130785 discloses an alternative process in which tetrachlorosilane, a polycyclic secondary amine, and an alcohol are reacted in the presence of a hydrogen chloride-trapping reagent such as an amine compound, to prepare a di(polycyclic amino) dialkoxysilane.

Japanese Patent Provisional Publication No. 11-158190 discloses another alternative process in which tetrachlorosilane, a polycyclic secondary amine, and an alkali metal alkoxide or an alkaline earth metal alkoxide are reacted in the presence of the hydrogen chloride-trapping reagent, to prepare a di(polycyclic amino)dialkoxysilane.

The latter two preparing processes utilizing no Grignard reaction have disadvantageous features in that a relatively great amount of impurities are produced and the yield of the target compound is relatively low.

It is an object of the present invention to provide a process for preparing (polycyclic secondary-amino)dialkoxysilanes with a high purity and a high yield.

SUMMERY OF THE INVENTION

The present invention resides in a process for preparing a (polycyclic secondary-amino)dialkoxysilane which comprises the steps of:

reacting tetrachlorosilane or a mono($C_1$–$C_8$) alkyltrichlorosilane with a polycyclic secondary-amine in an essentially non-hydrous, non-alcoholic organic solvent in the presence of a hydrogen chloride-trapping reagent, to produce a (polycyclic secondary-amino)chlorosilane; and reacting the (polycyclic secondary-amino)chlorosilane with an alkali metal alkoxide or an alkaline earth metal alkoxide in the presence of a lower alcohol.

The reactants and the products in the reaction adopted in the reaction of the process of the invention can be stated by chemical formulas as follows:

Tetrachlorosilane: $SiCl_4$

Mono($C_1$–$C_8$)alkyltrichlorosilane: $R^1_m SiCl_3$ (Polycyclic secondary-amino)chlorosilane: $R_k R^1_m SiCl_2$ (Polycyclic secondary-amino)dialkoxysilane: $R_k R^1_m Si(OR^2)_2$ In the above-mentioned formulas, R represents a polycyclic secondary-amino group, each of $R^1$ and $R^2$ independently represents a hydrocarbyl group having 1 to 8 carbon atoms, k is 1 or 2, and m is 0 or 1.

DETAILED DESCRIPTION OF THE INVENTION

The steps of the process according to the invention are further described below in more detail.

The first step are directed to the preparation of a (polycyclic secondary-amino)chlorosilane by reacting tetrachlorosilane or a mono($C_1$–$C_8$)alkyltrichlorosilane with a polycyclic secondary-amine in an essentially nonhydrous, non-alcoholic organic solvent in the presence of a hydrogen chloride-trapping reagent.

Representative polycyclic secondary amines are polycyclic perhydro secondary amines. Their examples include amine compounds having cyclohexyl ring such as perhydroindole, perhydroisoindole, perhydroquinoline, perhydroisoquinoline, perhydrocarbazole, perhydroiminostilbene, perhydroacridine, and perhydrobenzo [f] quinoline, perhydrobenzo [g] quinoline, perhydrobenzo [g] isoquinoline, and perhydrophenanthoridine. One or more substituents such as alkyl, phenyl, and cycloalkyl can be attached to the carbon atom(s) of the cyclohexyl ring.

Preferable polycyclic secondary amines are perhydroindole, perhydroisoindole, perhydroquinoline, perhydroisoquinoline, and their derivatives having one or more substituents. These polycyclic secondary-amines can be in the cis form, in the trans form, and in their mixture.

The mono($C_1$–$C_8$)alkyltrichlorosilane preferably is methyltrichlorosilane and ethyltrichlorosilane. Tetrachlorosilane is also preferred.

The reaction solvent is a non-alcoholic organic solvent. Their examples include inert hydrocarbon solvents such as pentane, hexane, heptane, octane, cyclohexane, benzene, toluene and hexane and non-alcoholic polar organic solvents having no active hydrogens such as ethers, ketones, esters, and amines. The hydrocarbon solvents are preferred so as to readily separate and recover a salt of the hydrogen chloride-trapping reagent with by-produced hydrogen chloride from the reaction mixture. Preferred are low boiling-point solvents such as pentane, hexane, and heptane.

The non-alcoholic organic solvent to be employed in the reaction should be essentially anhydrous. The term of "essentially anhydrous" is used to mean the water content of not more than 1 wt. %, specifically not more than 0.1 wt. %, more specifically not more than 0.03 wt. %.

The hydrogen chloride-trapping reagent can be any basic nitrogen containing compound or any phosphorus compound. Examples are amines, amides, imines, nitriles, and oximes. Preferred examples of the hydrogen chloride-trapping reagents include trimethylamine, triethylamine, tripropylamine, tributylamine, trihexylamine, dimethylphenylamine, triphenylamine, N-methylpyrolidine, N-methylpiperidine, and their derivatives. Preferred examples also include aromatic heterocyclic compounds such as pyridine, quinoline, isoquinoline, and their derivatives. Most preferred is triethylamine.

Alternatively, the polycyclic secondary amine, which is one of the starting compounds in the first step, can be employed in an excessive amount so that the additional secondary amine can serve as the hydrogen chloride-trapping reagent.

In performing the reaction of the first step, tetrachlorosilane or monoalkyltrichlorosilane is preferably brought into contact with a polycyclic secondary amine in the presence of a hydrogen chloride-trapping reagent. For instance, it is preferred that a mixture of a hydrogen chloride-trapping reagent and a polycyclic secondary amine is dropwise added to a reaction solvent containing the chlorosilane compound.

The reaction of the first step is ordinarily performed at a temperature of −30 to 100° C., preferably at −10 to 60° C., ordinarily for a period of 1 to 1,000 minutes, preferably for 5 to 500 minutes.

The (polycyclic secondary-amino)chlorosilane can be represented by the formula of $R_kR^1_mSiCl_2$ (R is a polycyclic secondary-amino group, $R^1$ is a hydrocarbyl group having 1 to 8 carbon atoms, k is 1 or 2, and m is 0 or 1). Examples are bis(polycyclic secondary amino)dichlorosilanes and alkyl(polycyclic secondary amino)dichlorosilanes.

Examples of the (polycyclic secondary-amino) chlorosilanes include bis(perhydroindolino)dichlorosilane, bis(perhydroisoindolino)dichlorosilane, bis(perhydroquinolino)dichlorosilane, bis(perhydroisoquinolino)dichlorosilane, methyl(perhydroindolino)dichlorosilane, methyl(perhydroisoindolino)dichlorosilane, methyl(perhydroquinolino)dichlorosilane, methyl(perhydroisoquinolino)dichlorosilane, ethyl(perhydroindolino)dichlorosilane, ethyl(perhydroisoindolino)dichlorosilane, ethyl(perhydroquinolino)dichlorosilane, ethyl(perhydroisoquinolino)dichlorosilane, n-propyl(perhydroindolino)dichlorosilane, n-propyl(perhydroisoindolino)dichlorosilane, n-propyl(perhydroquinolino)dichlorosilane, n-propyl(perhydroisoquinolino)dichlorosilane, isopropyl(perhydroindolino)dichlorosilane, isopropyl(perhydroisoindolino)dichlorosilane, isopropyl(perhydroquinolino)dichlorosilane, isopropyl(perhydroisoquinolino)dichlorosilane, n-butyl(perhydroindolino)dichlorosilane, n-butyl(perhydroisoindolino)dichlorosilane, n-butyl(perhydroquinolino)dichlorosilane, n-butyl(perhydroisoquinolino)dichlorosilane, isobutyl(perhydroindolino)dichlorosilane, isobutyl(perhydroisoindolino)dichlorosilane, isobutyl(perhydroquinolino)dichlorosilane, isobutyl(perhydroisoquinolino)dichlorosilane, sec-butyl(perhydroindolino)dichlorosilane, sec-butyl(perhydroisoindolino)dichlorosilane, sec-butyl(perhydroquinolino)dichlorosilane, sec-butyl(perhydroisoquinolino)dichlorosilane, ter-butyl(perhydroindolino)dichlorosilane, ter-butyl(perhydroisoindolino)dichlorosilane, ter-butyl(perhydroquinolino)dichlorosilane, ter-butyl(perhydroisoquinolino)dichlorosilane, cyclopentyl(perhydroindolino)dichlorosilane, cyclopentyl(perhydroisoindolino)dichlorosilane, cyclopentyl(perhydroquinolino)dichlorosilane, cyclopentyl(perhydroisoquinolino)dichlorosilane, cyclohexyl(perhydroindolino)dichlorosilane, cyclohexyl(perhydroisoindolino)dichlorosilane, cyclohexyl(perhydroquinolino)dichlorosilane, and cyclohexyl(perhydroisoquinolino)dichlorosilane.

In the course of the reaction of the first step, a salt of a hydrogen chloride-trapping reagent and by-produced hydrogen chloride is produced in the reaction mixture. The reaction mixture containing the salt of hydrogen chloride-trapping reagent and by-produced hydrogen chloride can be directly subjected to the reaction of the second step. It is preferred, however, that the salt is removed from the reaction mixture before the reaction mixture is subjected to the reaction of the second step. The removal of the salt from the reaction step can be performed by filtration or a combination of extraction with an aqueous solvent and separation of the aqueous extract.

In the second procedure, the reaction mixture of the first step is mixed with water, so as to dissolve the salt in water, and the water portion is separated. The remaining organic solution is then dehydrated and subjected to the reaction of the second step. The water to be mixed with the reaction mixture preferably is in such amount that the water dissolve the whole amount of the by-produced salt. The dehydration of the reaction mixture subjected to the extraction with water can be carried out using a dehydrating reagent such as molecular sieve. It is preferred that almost whole water content is removed from the reaction mixture.

In the second step, the (polycyclic secondary-amino) chlorosilane is caused to react with an alkali metal alkoxide or an alkaline earth metal alkoxide in the presence of a lower alcohol. Generally, the reaction mixture obtained in the first step per se is, directly or after removal of the by-produced salt, subjected to the second step. A portion of the solvent of the reaction mixture can be removed, or an essentially non-hydrous organic solvent can be added.

The alkali metal can be sodium or potassium. The alkaline earth metal can be magnesium or calcium. The alkoxide can be methoxide or ethoxide. Sodium methoxide is most preferred.

The lower alcohol employed in the second step preferably is methanol, ethanol, or propanol. Methanol is most preferred.

The alkali metal alkoxide or alkaline earth metal alkoxide is preferably employed in the form of an alcoholic solution, particularly a homogeneous alcoholic solution. In the alcoholic solution, the alkoxide is generally contained in an amount of 10 wt. % or more, preferably in an amount of 20 wt. % or more. Most preferred is a concentration in the range of 20 to 40 wt. %.

It is preferred that a solution of sodium methoxide in methanol is employed in the reaction of the second step.

The alcoholic solution of an alkali metal alkoxide or an alkaline earth metal alkoxide can be produced by dissolving the alkali metal alkoxide or alkaline earth metal alkoxide in a lower alcohol. In place of the alkali metal alkoxide or alkaline earth metal alkoxide, an alkali metal hydride, an alkaline earth metal hydride, an organic alkali metal compound, or an organic alkaline earth metal compound can be dissolved in a lower alcohol.

Examples of the alkali metal or alkaline earth metal hydrides include lithium hydride, sodium hydride, and magnesium hydride. Examples of the organic alkali metal compounds include butyl lithium, phenyl lithium, and cyclopentadienyl sodium. Examples of the organic alkaline earth metal compounds include dialkylmagnesiums such as dibutylmagnesium, butylethylmagnesium, and dihexylmagnesium, and Grignard compounds such as alkylmagnesium chloride, alkylmagnesium bromide, and alkylmagnesium iodide. In the Grignard compounds, the alkyl can be methyl, ethyl, propyl, butyl, hexyl, or octyl.

The hydrogen chloride-trapping reagent, polycyclic secondary amines, alkali metal or alkaline earth metal alkoxide, and reaction solvents employed in the reactions of the invention are also preferred to have a water content as small as possible.

The reaction of the second step is ordinarily carried out at a temperature of −30 to 100° C., preferably at −10 to 80° C., more preferably 0 to 70° C., ordinarily for a period of 1 to 1,000 minutes, preferably for 3 to 500 minutes.

In the case that triethylamine is employed as the hydrogen chloride-trapping agent, a molar ratio of the chlorosilane compound/polycyclic secondary amine ordinarily is in the range of 0.3 to 1.3, preferably 0.4 to 1.2. The polycyclic secondary amine can be employed singly or in combination of two amines. In the case that two polycyclic secondary amines are employed in combination, a molar ratio of the chlorosilane compound/one polycyclic secondary amine ordinarily is in the range of 0.9 to 1.1, preferably 0.95 to 1.05. The polycyclic secondary amine can be employed singly or in combination of two amines. In the case that the polycyclic secondary amine is employed in excessive amount so that a portion of the amine can serve as the hydrogen chloride-trapping reagent, a molar ratio of the chlorosilane compound/polycyclic secondary amine ordinarily is in the range of 0.1 to 0.6, preferably 0.15 to 0.55.

The hydrogen chloride-trapping reagent is employed at a molar ratio of generally 0.3 to 1.5, preferably 0.4 to 1.35, in terms of chlorosilane compound/hydrogen chloride-trapping reagent. The alkali metal alkoxide or alkaline earth metal alkoxide is employed at a molar ratio of generally 0.1 to 0.6, preferably 0.15 to 0.55, in terms of chlorosilane compound/alkoxide.

As describe hereinbefore, when the second step is started after completion of the first step, the salt of a hydrogen chloride-trapping reagent and by-produced hydrogen chloride formed in the reaction of the first step can be separated. The separated salt can be neutralized with an aqueous alkaline solution such as an aqueous sodium hydroxide solution to recover the hydrogen chloride-trapping reagent. The recovered reagent may be then purified for the use as the hydrogen-trapping reagent.

According to the process of the invention, a bis(polycyclic perhydroamino)dialkoxysilane is produced when tetrachlorosilane is employed, while an alkyl(polycyclic perhydroamino)dialkoxysilane is produced when a monoalkyltrichlorosilane is employed.

Representative bis(polycyclic perhydroamino)dialkoxysilanes are bis(polycyclic perhydroamino)dimethoxysilanes such as bis(perhydroisoquinolino)dimethoxysilane, bis(perhydroquinolino)dimethoxysilane, bis(perhydroindolino)dimethoxysilane, and bis(perhydroisoindolino)dimethoxysilane.

The bis(polycyclic perhydroamino)dimethoxysilane can be present in geometric isomers such as cis-form and trans-form. Therefore, there are three geometric isomers such as bis(cis-polycyclic perhydroamino)dimethoxysilane, bis(trans-polycyclic perhydroamino)dimethoxysilane, and (cis-polycyclic perhydroamino)(trans-polycyclic perhydroamino)dimethoxysilane. In the case of bis(perhydroisoquinolino)dimethoxysilane, there are three geometric isomers, i.e., bis(cis-perhydroisoquinolino)dimethoxysilane, bis(trans-perhydroisoquinolino)dimethoxysilane, and (cis-perhydroisoquinolino)(trans-perhydroisoquinolino)dimethoxysilane.

Representative examples of the alkyl(polycyclic perhydroamino)dialkoxysilanes are alkyl(polycyclic perhydroamino)dimethoxysilanes. Examples of the alkyl(polycyclic perhydroamino)dimethoxysilanes include methyl(perhydroindolino)dimethoxysilane, methyl(perhydroisoindolino)dimethoxysilane, methyl(perhydroquinolino)dimethoxysilane, methyl(perhydroisoquinolino)dimethoxysilane, ethyl(perhydroindolino)dimethoxysilane, ethyl(perhydroisoindolino)dimethoxysilane, ethyl(perhydroquinolino)dimethoxysilane, ethyl(perhydroisoquinolino)dimethoxysilane, n-propyl(perhydroindolino)dimethoxysilane, n-propyl(perhydroisoindolino)dimethoxysilane, n-propyl(perhydroquinolino)dimethoxysilane, n-propyl(perhydroisoquinolino)dimethoxysilane, isopropyl(perhydroindolino)dimethoxysilane, isopropyl(perhydroisoindolino)dimethoxysilane, isopropyl(perhydroquinolino)dimethoxysilane, isopropyl(perhydroisoquinolino)dimethoxysilane, n-butyl(perhydroindolino)dimethoxysilane, n-butyl(perhydroisoindolino)dimethoxysilane, n-butyl(perhydroquinolino)dimethoxysilane, n-butyl(perhydroisoquinolino)dimethoxysilane, isobutyl(perhydroindolino)dimethoxysilane, isobutyl(perhydroisoindolino)dimethoxysilane, isobutyl(perhydroquinolino)dimethoxysilane, isobutyl(perhydroisoquinolino)dimethoxysilane, sec-butyl(perhydroindolino)dimethoxysilane, sec-butyl(perhydroisoindolino)dimethoxysilane, sec-butyl(perhydroquinolino)dimethoxysilane, sec-butyl(perhydroisoquinolino)dimethoxysilane, ter-butyl(perhydroindolino)dimethoxysilane, ter-butyl(perhydroisoindolino)dimethoxysilane, ter-butyl(perhydroquinolino)dimethoxysilane, ter-butyl(perhydroisoquinolino)dimethoxysilane, cyclopentyl(perhydroisoindolino)dimethoxysilane, cyclopentyl(perhydroisoindolino)dimethoxysilane, cyclopentyl(perhydroisoquinolino)dimethoxysilane, cyclohexyl(perhydroindolino)dimethoxysilane, cyclohexyl(perhydroisoindolino)dimethoxysilane, cyclohexyl(perhydroquinolino)dimethoxysilane, and cyclohexyl(perhydroisoquinolino)dimethoxysilane.

The present invention is further described by the following examples.

In the following examples, the reaction products were gas chromatographically analyzed using the apparatuses described below.

GC-14A (Shimazu Seisakusho Co., Ltd.), FID detector, glass capillary column: G-100 (20 m), column temperature: 100° C. to 260° C., rate of temperature elevation: 20° C./min., detector temperature: 280° C., injection temperature: 280° C., carrier gas: helium (flow rate: 50 mL/min.)

EXAMPLE 1

An inner space of a 500 mL-volume flask equipped with a dropping funnel and a stirring fan is purged with nitrogen gas. In the flask were then placed 240 mL of n-heptane (distilled and dehydrated) and 3.4 g (20 mmol.) of tetrachlorosilane. Through the dropping funnel, a mixture of 20 mL of n-heptane (distilled and dehydrated), 5.6 g (40 mmol.) of perhydroisoquinoline (mixture of cis-form (75 molar %) and trans-form (25 molar %)) and 4.6 g (45 mmol.) of triethylamine (hydrogen chloride-trapping reagent) was dropwise placed into the flask under chilling with ice. The mixture in the flask was stirred for 2 hours.

The reaction mixture was filtered on a glass filter (G4), and the residue on the filter was washed three portions of n-heptane (20 mL). The filtrate and washings were combined and placed again in the same flask equipped with a dropping funnel and a stirring fan. Into the flask was dropwise placed through the dropping funnel a methanol solution of sodium methoxide (28 wt. % solution), until 40 mmol. of sodium methoxide was introduced into the flask. The mixture was then stirred at 25° C. for 8 hours. The reaction mixture was concentrated and then placed under reduced pressure to recover the reaction product by distillation.

There was obtained bis(perhydroisoquinolino) dimethoxysilane (colorless clear liquid, b.p.: 180° C./1 mmHg). Yield: 94.5% (on the basis of Si content). Purity: 98.5% (determined gas chromatographically).

The residue on the filter was triethylamine hydrochloride, and triethylamine was recovered by decomposition using 10 mL of 5% aqueous sodium hydroxide solution.

EXAMPLE 2

The procedures of Example 1 were repeated except that the mixture produced by addition of the methanolic sodium methoxide solution was stirred at 60° C. for 3 hours, to obtain bis(perhydroisoquinolino)dimethoxysilane (colorless clear liquid). Yield: 95.3% (on the basis of Si content). Purity: 99.5% (determined gas chromatographically).

The residue on the filter was triethylamine hydrochloride, and triethylamine was recovered by decomposition using 10 mL of 5% aqueous sodium hydroxide solution.

EXAMPLE 3

The procedures of Example 1 were repeated except that triethylamine (hydrogen chloride-trapping reagent) was not used while perhydroisoquinoline was used in a double amount (11.2 g, 80 mmol.), to obtain bis (perhydroisoquinolino)dimethoxysilane (colorless clear liquid). Yield: 92.1% (on the basis of Si content). Purity: 97.7% (determined gas chromatographically).

The residue on the filter was triethylamine hydrochloride, and triethylamine was recovered by decomposition using 10 mL of 5% aqueous sodium hydroxide solution.

EXAMPLE 4

The procedures of Example 1 were repeated except for replacing perhydroisoquinoline with perhydroquinoline (mixture of cis-form (50 molar %) and trans-form (50 molar %),to obtain bis(perhydroquinolino)dimethoxysilane (colorless clear liquid, b.p.: 189.5° C./1 mmHg)). Yield: 90.1% (on the basis of Si content). Purity: 97.9% (determined gas chromatographically).

The residue on the filter was triethylamine hydrochloride, and triethylamine was recovered by decomposition using 10 mL of 5% aqueous sodium hydroxide solution.

EXAMPLE 5

The procedures of Example 4 were repeated except for replacing the filtration of the residue produced in the first reaction with the below-mentioned separation procedure, to obtain bis(perhydroquinolino)dimethoxysilane (colorless clear liquid). Yield: 88.6% (on the basis of Si content). Purity: 98.0% (determined gas chromatographically).

Separation procedure: Under chilling with ice, 150 mL of distilled water is added to the reaction mixture, to dissolve triethylamine hydrochloride in the water. The mixture separates into an aqueous layer and a heptane layer. The heptane layer is recovered using a separating funnel. The heptane layer is immediately introduced into a flask containing 100 cc of a synthetic zeolite adsorbent (Zeolam, ball, 3A). The content is quickly stirred, and filtered.

EXAMPLE 6

An inner space of a 500 ml-volume flask equipped with a dropping funnel and a stirring fan is purged with nitrogen gas. In the flask were then placed 240 mL of n-heptane (distilled and dehydrated) and 6.8 g (40 mmol.) of tetrachlorosilane. Through the dropping funnel, a mixture of 20 mL of n-heptane (distilled and dehydrated), 11.2 g (80 mmol.) of perhydroquinoline (mixture of cis-form (50 molar %) and trans-form (50 molar %)) and 9.2 g (90 mmol.) of triethylamine (hydrogen chloride-trapping reagent) was dropwise placed into the flask under chilling with ice. The mixture in the flask was stirred for 2 hours.

Under chilling with ice, 150 mL of distilled water was added to the reaction mixture, to dissolve triethylamine hydrochloride in the water. The mixture separated into an aqueous layer and a heptane layer. The heptane layer was recovered using a separating funnel. The heptane layer was immediately introduced into a flask containing 100 cc of a synthetic zeolite adsorbent (Zeolam, ball, 3A). The content was quickly stirred, and filtered. The filtrate was placed again in the same flask equipped with a dropping funnel and a stirring fan.

Into the flask was dropwise placed through the dropping funnel a methanol solution of sodium methoxide (28 wt. % solution), until 80 mmol. of sodium methoxide was introduced into the flask. The mixture was then stirred at 25° C. for 8 hours. The reaction mixture was concentrated and then placed under reduced pressure to recover the reaction product by distillation.

There was obtained bis(perhydroquinolino) dimethoxysilane (colorless clear liquid). Yield: 89.9% (on the basis of Si content). Purity: 98.8% (determined gas chromatographically).

EXAMPLE 7

The procedures of Example 1 were repeated except that tetrachlorosilane was replaced with ethyltrichlorosilane (3.3 g, 20 mmol.), the distilled and dehydrated n-heptane was added in an amount of 10 mL, perhydroisoquinoline was employed in an mount of 2.8 g (20 mmol.) and triethylamine was added in an amount of 2.6 g (25 mmol.), to obtain ethyl(perhydroisoquinolino)dimethoxysilane (colorless clear liquid, b.p.: 120–125° C./0.3 mmHg). Yield: 92.2% (on the basis of Si content). Purity: 98.9% (determined gas chromatographically).

The residue on the filter was triethylamine hydrochloride, and triethylamine was recovered by decomposition using 10 mL of 5% aqueous sodium hydroxide solution.

COMPARISON EXAMPLE 1

The procedures of Example 1 were repeated except that a mixture of 20 mL of n-heptane (distilled and dehydrated), 40 mL of methanol, and 4.6 g (45 mmol.) of triethylamine was added to the filtrate obtained in the first step, in place of the methanolic sodium methoxide solution (28 wt. %), to obtain bis.(perhydroisoquinolino)dimethoxysilane (colorless clear liquid). Yield: 77.7% (on the basis of Si content). Purity: 91.0% (determined gas chromatographically).

COMPARISON EXAMPLE 2

The procedures of Example 1 were repeated except that 40 mL of n-heptane slurry containing 20 mmol of sodium methoxide was added to the filtrate obtained in the first step, in place of the methanolic sodium methoxide solution (28 wt. %), to obtain bis(perhydroisoquinolino)dimethoxysilane (colorless clear liquid). Yield: 81.1% (on the basis of Si content). Purity: 90.8% (determined gas chromatographically).

What is claimed is:

1. A process for preparing a (polycyclic secondary-amino) dialkoxysilane which comprises the steps of:

reacting tetrachlorosilane or a mono($C_1$–$C_8$) alkyltrichlorosilane with a polycyclic secondary-amine in an essentially non-hydrous, non-alcoholic organic solvent in the presence of a hydrogen chloride-trapping reagent, to produce a (polycyclic secondary-amino) chlorosilane; and reacting the (polycyclic secondary-amino)chlorosilane with an alkali metal alkoxide or an alkaline earth metal alkoxide in the presence of a lower alcohol.

2. The process of claim 1, wherein the (polycyclic secondary-amino)chlorosilane produced in the non-alcoholic organic solvent is caused to react with the reaction with an alkali metal alkoxide or an alkaline earth metal alkoxide in the presence of a lower alcohol, without isolation from the organic solvent.

3. The process of claim 2, wherein a salt which is formed by a reaction between the hydrogen chloride-trapping reagent and hydrogen chloride produced in the reaction between the tetrachlorosilane or a mono($C_1$–$C_8$) alkyltrichlorosilane with a polycyclic secondary-amine is removed after the first step is complete.

4. The process of claim 3, wherein the removal of the salt is performed by filtration or a combination of dissolution of the salt in an aqueous solvent and removal of the aqueous solvent containing the salt.

5. The process of claim 1, wherein the non-alcoholic organic solvent is an aliphatic hydrocarbon having 5 to 8 carbon atoms.

6. The process of claim 1, wherein the lower alcohol is methanol or ethanol.

7. The process of claim 1, wherein the polycyclic secondary-amine is perhydroisoquinoline or perhydroquinoline.

8. The process of claim 1, wherein the mono($C_1$–$C_8$) alkyltrichlorosilane is methyltrichlorosilane or ethyltrichlorosilane.

* * * * *